United States Patent [19]
Hayashizaki

[11] Patent Number: 5,916,775
[45] Date of Patent: Jun. 29, 1999

[54] METHOD FOR THE PURIFICATION OF DNA

[75] Inventor: Yoshihide Hayashizaki, Ibaragi, Japan

[73] Assignee: The Institute of Physical and Chemical Research, Saitama, Japan

[21] Appl. No.: 08/877,874

[22] Filed: Jun. 18, 1997

[30] Foreign Application Priority Data

Jun. 18, 1996 [JP] Japan ..................................... 8-157245
Oct. 2, 1996 [JP] Japan ..................................... 8-261497

[51] Int. Cl.$^6$ ........................... C12P 19/34; C12N 13/00; C12N 11/00; C07H 21/04
[52] U.S. Cl. ..................... 435/91.1; 435/173.7; 435/182; 536/25.4
[58] Field of Search ........................... 435/6, 91.1, 173.7, 435/182; 536/23.1, 25.4

[56] References Cited

U.S. PATENT DOCUMENTS

| | | | |
|---|---|---|---|
| 5,057,426 | 10/1991 | Henco et al. ............................. | 435/270 |
| 5,438,128 | 8/1995 | Nieuwkerk et al. .................... | 536/25.4 |
| 5,652,141 | 7/1997 | Henco et al. ............................. | 435/270 |

FOREIGN PATENT DOCUMENTS

| | | |
|---|---|---|
| 0 389 063 | 3/1990 | European Pat. Off. . |
| 0517515 | 6/1992 | European Pat. Off. . |
| 07250681 | 3/1995 | European Pat. Off. . |
| 0 648 776 | 4/1995 | European Pat. Off. . |
| 4422044 | 12/1995 | Germany . |
| WO92/07863 | 5/1992 | WIPO . |
| WO93/11218 | 6/1993 | WIPO . |
| WO95/02049 | 1/1995 | WIPO . |
| WO95/21849 | 8/1995 | WIPO . |

OTHER PUBLICATIONS

J. Sambrook et al., "Molecular Cloning. A Laboratory Manual", vol. 1, Second edition, 1989, Cold Spring Harbor Laboratory Press, pp. 1.22–1.39.

Yokoyama–Kobayashi et al., "Recombinant f1 Phge–Mediated Transfection of Mammalian Cells Using Lipopolymine Technique", *Analytical–Biochemistry* (1994) 223:130–134.

Huang et al, "A High–Throughout Plasmid DNA Preparation Method", *Analytical Biochemistry* (1994) 223:35–38.

R. Boom et al, "Rapid and Simple Method for Purification of Nucleic Acids", J. Clin. Microbiol. (1990) 28:495–503, No. 3.

*Primary Examiner*—Nancy Degen
*Assistant Examiner*—William Sandals
*Attorney, Agent, or Firm*—Burns, Doane, Swecker & Mathis, L.L.P.

[57] ABSTRACT

Disclosed is a method for collecting DNA by lysing microbial cells, adsorbing released DNA on a carrier and collecting the DNA adsorbed on the carrier, which method comprises the following steps of (1) lysing the microbial cells in the presence of the carrier so that the DNA obtained by lysing cells is adsorbed onto the carrier, separating solutions used for lysing cells and adsorbing DNA from the carrier, and eluting the DNA adsorbed on the carrier with a solution for eluting DNA and collecting eluted DNA, or (2) feeding microbial cells into a column comprising the carrier provided on a membrane filter capable of retaining a solution and permeating the solution when aspirated, lysing the microbial cells in the column so that the DNA obtained by lysing cells is adsorbed onto the carrier, separating solutions used for lysing cells and adsorbing DNA in the previous step from the column by aspiration, and feeding a solution for eluting DNA into the column and aspirating to collect the DNA adsorbed on the carrier. The methods of the present invention enable collection of DNA by the chaotropic ion method employing an apparatus with simpler structure and fewer operations.

25 Claims, No Drawings

METHOD FOR THE PURIFICATION OF DNA

BACKGROUND OF THE INVENTION

The present invention relates to a method for collecting DNA contained in microorganisms.

In the genetic engineering, plasmid DNA is isolated from microorganisms by transforming microorganisms such as *E. coli,* culturing the transformants and collecting des red plasmid DNA from the amplified transformants.

However, collection and purification of plasmid DNA from transformants require several steps and are tedious. Many improvements have been proposed in methods for purification of plasmid DNA.

For example, Japanese Patent Unexamined Publication No. Hei 4-360686 (JP-A-360686/92) discloses a method for the purification of plasmid DNA and/or cosmid DNA by lysing microbial cells, filtering the resulting lysate with a membrane filter to remove insolubles and subjecting the filtrate to ultrafiltration to remove impurities and concentrate the DNA.

Japanese Patent Unexamined Publication No. Hei 8-23976 (JP-A-23976/96) discloses a method for purifying supercoiled plasmid by removing impurities from a plasmid mixture using a filtration filter having an average pore diameter of 10 nm to 35 nm.

In these methods, however, the resulting purified DNA may contain RNA, which has been contained in the microbial cells together with the DNA, and an additional step is required to degrade the RNA to provide DNA without contamination.

There has been known a method for separating RNA and DNA utilizing a carrier capable of adsorbing DNA together with a chaotropic solution (Chaotropic Ion Method) (R. Room et al,. J. Clin. MicroBiol. Vol.28, No.3, p495–503). Japanese Patent Unexamined Publication No. Hei 7-250681 (JP-A-250681/95) discloses a method for purifying DNA in which RNA contained in microbial cells with the DNA is removed by the above method.

This method is one for extracting and purifying plasmid DNA comprising steps of collecting microbial cells from a culture of transformants into a first cartridge, lysing the cells and separating undesired RNA, filtering off impurities by the first cartridge, and adsorbing, washing and eluting the DNA by a second cartridge.

However, this method requires two cartridges, and the first cartridge should have at least a trap filter and a membrane filter, and the second should have at least a glass fiber filter, glass powder layer and membrane filter. These cartridges are structurally more complex compared to a simple filter itself. In addition, this method requires repetitive feeding and draining of the solution by aspiration using the two cartridges.

Therefore, an object of the present invention is to provide a method for collecting DNA by the Chaotropic Ion Method with an apparatus with simpler structure and fewer operations.

SUMMARY OF THE INVENTION

The present invention relates to a method for collecting DNA by lysing microbial cells, adsorbing released DNA on a carrier and collecting the DNA adsorbed on the carrier, which method comprises the following steps of:

lysing the microbial cells in the presence of the carrier so that the DNA obtained by lysing cells is adsorbed onto the carrier, separating solutions used for lysing cells and adsorbing DNA from the carrier, and eluting the DNA adsorbed on the carrier with a solution for eluting DNA and collecting eluted DNA (The first method of the present invention).

The present invention further relates to a method for collecting DNA by lysing microbial cells, adsorbing released DNA on a carrier and collecting the DNA adsorbed on the carrier, which method comprises the following steps of:

feeding microbial cells into a column comprising the carrier provided on a membrane filter capable of retaining a solution and permeating the solution when aspirated, lysing the microbial cells in the column so that the DNA obtained by lysing cells is adsorbed onto the carrier, separating solutions used for lysing cells and adsorbing DNA from the column by aspiration, and feeding a solution for eluting DNA into the column and aspirating to collect the DNA adsorbed on the carrier (The second method of the present invention).

DESCRIPTION OF THE INVENTION

The present invention will be explained more in detail hereinafter.

Both of the first and the second methods of the present invention are a method for collecting DNA by lysing microbial cells, adsorbing released DNA on a carrier and collecting the DNA adsorbed on the carrier.

The objective microbial cells for the methods of the present invention are not particularly limited and any microbial cells containing desired DNA may be used. For example, the microbial cells may be transformants obtained by introducing a desired DNA into host microorganisms.

In the methods of the present invention, (1) lysis of microbial cells and (2) adsorption of released DNA onto a carrier and elution thereof may be performed in a conventional manner.

However, the methods of the present invention are characterized in that the lysis of microbial cells and the adsorption of DNA released by the lysis onto a carrier are performed in a one pot operation.

According to the first method of the present invention, DNA is adsorbed on a carrier by successively adding a solution for lysing microbial cells and a solution for DNA adsorption to microbial cells in the presence of the carrier, or DNA is adsorbed on a carrier by successively adding a solution for lysing microbial cells and a solution for neutralization and DNA adsorption to microbial cells in the presence of the carrier.

In the presence of a solution for containing chaotropic ions, glass adsorbs DNA but not RNA (R. Room et al,. J. Clin. MicroBiol. Vol. 28, No.3, p495–503). Examples of the carrier include glasses, silica gels, anion exchange resins and celite such as Diatomaceous Earth. The shape of the carrier is not particularly limited, but it preferably has a large surface area for adsorption. The carrier may be in the form of mesh filter, beads or powder. For example, it may be in the form of glass filter, glass beads and glass powder.

The solution for DNA adsorption is a solution containing chaotropic ions. The solution for lysing microbial cells may consist of a solution for degrading microbial cell walls (Solution I), a solution of alkaline-ionizable surfactant (Solution II) and a neutralization solution (Solution III), or a solution for degrading microbial cell walls (Solution I) and a solution of alkaline-ionizable surfactant (Solution II). In the latter case, when the solution for lysing microbial cells is composed of Solution I and Solution II, the solution for neutralization and DNA adsorption which is a single solution containing a neutralizer and chaotropic ions is used.

The solution for degrading microbial cell walls (Solution I) has a function to make the microbial cells into spheroplasts and it may be, for example, an aqueous solution of Tris/EDTA/glucose/lysozyme (Solution I). The solution of alkaline-ionizable surfactant (Solution II) has functions to cause lysis of microbial cells by dissolving membranes and proteins of the cells and to denature DNA and it may be, for example, an aqueous solution of NaOH/SDS (Solution II). The neutralization solution (Solution III) has a function to neutralize the solution made alkaline with Solution II and it may be, for example, an aqueous solution of potassium acetate. The cell lysis can be performed by successively adding these three kinds or two kinds of solutions to microbial cells. The concentration and the amount of each solution can be adequately determined in view of the nature and the amount of microbial cells and the like.

It is advantageous to use the solution for neutralization and DNA adsorption which is a solution containing a neutralizer (e.g., potassium acetate) and chaotropic ions, because it enables concurrent neutralization of the solution and DNA adsorption and hence it can shorten the process time. When a solution containing a neutralizer and chaotropic ions is used as the solution for DNA adsorption, it is preferred that the pH of the solution is adjusted to a range of 6–12 because such a pH range can prevent contamination of RNA. The desired pH value may vary depending on ionic strength and be appropriately selected in view of the conditions used. It is also possible to add RNase into Solution I in order to prevent the RNA contamination.

The solution for DNA adsorption and the solution for neutralization and DNA adsorption may be, for example, an aqueous solution containing $LiClO_4$, KI, NaI, LiCl, NaCOOH, guanidine hydrochloride or the like as chaotropic ions. The concentration, amount to be used and the like of the chaotropic solution may be appropriately decided in view of the nature and the amount of the bacterial cells. The solution for DNA adsorption or the solution for DNA adsorption is added to a mixture of the microbial cells and the solution for lysing microbial cells previously added in the presence of a carrier. By adding the solution for DNA adsorption, the DNA dissolved from the microbial cells is adsorbed onto the carrier.

The method of the present invention is characterized in that each solution to be added is fed successively without separating a previously fed solution, i.e., it does not require separation of solution for each addition of the solutions.

For the addition of the solutions, one solution is preferably fed 1 second to 60 minutes after the previous addition of solution to ensure that each solution exerts each function.

Then, the carrier adsorbing the DNA is separated from the solutions. The separation of the carrier from the solutions can be achieved by, for example, decantation, centrifugation, filtration or the like. The carrier which has been separated from the solutions may be washed and dried, if necessary. For such washing, for example, a mixture of Tris/EDTA/NaCl/ethanol, ethanol, a mixture of ethanol/glycerol and the like can be used.

Then, the DNA adsorbed on the carrier is eluted with the solution for eluting DNA and collected. For example, a Tris/EDTA buffer solution may be used as the solution for eluting DNA.

In the second method of the present invention, a column comprising a carrier provided on a membrane filter capable of retaining a solution and permeating the solution when aspirated is used. By using such a column, the separation and the collection can be performed more conveniently. When a plurality of samples of small volumes are processed simultaneously, a plurality of bundled columns can be used. Such columns may be a plate having a plurality of penetrated holes (wells), a membrane filter provided over openings of the holes on the one side of the plate and carriers filled in the holes.

The membrane filter is not particularly limited so long as it enables to retain a solution and to permeate the solution when aspirated. A commercially available membrane filter can be used as it is. The carrier explained above for the first method may be used in the second method. The size, shape and the like of the column can be decided suitably in view of the amounts of microbial cells to be treated and solutions to be used. Glass and Diatonaceous Earth ect. can be listed up as the carrier.

Microbial cells are fed into the column mentioned above. The feed microbial cells may be those separated from a culture broth by filtration, centrifugation or the like, or the microbial cells maybe fed by feeding a culture broth containing microbial cells as it is and aspirating the broth so that the microbial cells are trapped by the membrane filter.

Subsequently, the solution for lysing microbial cells and the solution for DNA adsorption are successively added to the column, or the solution for lysing microbial cells and the solution for neutralization and DNA adsorption are successively added to the column, so that the DNA is adsorbed on the carrier, such as glass carrier. The solution for lysing microbial cells, the solution for DNA adsorption and the solution for neutralization and DNA adsorption explained above for the first method may be employed in the second method. As already mentioned above, the methods of the present invention are characterized in that each solution to be added is fed successively without separating a previously fed solution and it does not require separation of solution for each feed of the solutions.

After the feed of all solutions, the solutions are removed from the column by aspiration through the membrane filter. By this operation, residue of microbial cells is left on the filter as well the DNA adsorbed on the carrier is remained on the filter. Subsequently, after optional washing for the removal of contaminants such as free RNA and proteins, the column including the carrier can be dried. To obtain the DNA with a higher purity, it is preferred that such washing as mentioned above is performed. For example, a mixed solution of Tris/EDTA/NaCl/ethanol, ethanol, a mixed solution of ethanol/glycerol and the like can be used for the washing.

Then, the solution for eluting DNA is fed to the column and the DNA adsorbed on the carrier is collected by aspiration. For example, a Tris-EDTA buffer solution can be used as the solution for eluting DNA.

Both of the first and the second methods of the present invention comprise the three steps of (1) successively adding the solution for lysing microbial cells and the solution for DNA adsorption, (2) separating the carrier from the solutions and (3) eluting DNA from the carrier. They enable the collection of DNA from microbial cells by these three steps. Further, it is preferred that a washing step for removing concomitants is provided before the elution of DNA so that a higher purity of the collected DNA is obtained.

DNA collected by the methods of the present invention is a double-stranded circular plasmid DNA including cosmid DNA, Bacterial Artificial Chromosome (BAC) and Pl-derived Artificial Chromosome (PAC).

EXAMPLES

The present invention will be further explained in more detail with reference to the following examples.

Example 1

*E. coli* SOLR strain harboring plasmid pbluescript SK (+) inserted with a 5.6 kb mouse CDNA was cultured overnight in LB culture medium containing 100 μg/ml of ampicillin. 0.6 ml of the culture medium was fed to each of 96 wells closed one of openings with a membrane and filled with glass filters, and the medium was filtered by aspiration so that microbial cells are trapped in the glass filter. To each well containing the microbial cells, 25 μl of Solution I (50 mM glucose, 25 mM Tris/HCl buffer [pH 8.0], 10 mM EDTA, 10 mg/ml of lysozyme) was added and left for 5 minutes. Then, 50 μl of Solution II (0.2N sodium hydroxide, 1% sodium dodecyl sulfate) was added and left for 5 minutes. Thereafter, 37.5 μl of Solution III (3M potassium acetate [pH 4.8]) was further added and left for 5 minutes. Then, 120 μl of 7M guanidine hydrochloride solution (solution for adsorption) was added and the medium was filtered by aspiration.

Subsequently, the residue was washed twice with 300 μl of a washing buffer (100 mM Tris/HCl buffer [pH 8.0], 5 mM EDTA, 0.2M sodium chloride, 60% ethanol), once with 300 μl of 80% ethanol and once with 300 μl of 100% ethanol and collected by filtration with aspiration after each washing. Then, plasmid DNA on the glass filter was dried by aspirating for 20 minutes. Finally, 25–50 μl of a TE buffer (10 mM Tris/HCl [pH8.0], 1 mM EDTA) warmed to65° C. was added and aspirated to elute the plasmid DNA.

As a result of the above procedures, 4–6 μg of the plasmid DNA was obtained. The plasmid DNA exhibited such a high purity that the absorbance ratio 260 nm vs. 280 nm is around 2 and could be satisfactorily used for DNA sequencing by the dideoxy method.

Example 2

*E. coli* SOLR strain harboring plasmid pBluescript SK (+) inserted with a 5.6 kb mouse CDNA was cultured overnight in LB culture medium containing 100 μg/ml of ampicillin. 0.6 ml of the culture medium was transferred to each of 96 wells closed one of openings with a membrane and filled with glass filters, and the medium was filtered by aspiration so that microbial cells are trapped in the glass filter. To each well containing the microbial cells, 25 μl of Solution I (50 mM glucose, 25 mM Tris/HCl buffer [pH8.0], 10 mM EDTA, 10 mg/ml of lysozyme) was added and left for 5 minutes. Then, 50 μl of Solution II (0.2N sodium hydroxide, 1% sodium dodecyl sulfate) was added and left for 5 minutes. Thereafter, 160 μl of solution for neutralization and adsorption (0.7M potassium acetate [pH4.8] and 5.3M guanidine hydrochloride solution) was further added and left for 5 minutes.

Subsequently, the mixed solution was filtered by aspiration from the wells and the residue was washed three times with 300 μl of 80% ethanol and once with 300 μl of 80% ethanol/20% glycerol. Then, plasmid DNA on the glass filter was dried by aspirating for 20 minutes. Finally, 25–50 μl of a TE buffer (10 mM Tris/HCl [pH8.0], 1 mM EDTA) warmed to 65° C. was added and aspirated to elute the plasmid DNA.

As a result of the above procedures, 4–6 μg of the plasmid DNA was obtained. The plasmid DNA exhibited such a high purity that the absorbance ratio 260 nm vs. 280 nm is around 2 and could be satisfactorily used for DNA sequencing by the dideoxy method. Further, because a mixed solution of potassium acetate and guanidine hydrochloride was used as the solution for neutralization and adsorption, the process time could be shortened by about 15 minutes compared to Example 1. In addition, the amount of the collected plasmid DNA was advantageously improved compared to Example 1 by using 80% ethanol/20% glycerol for washing, because the 80% ethanol/20% glycerol leads to better permeation of the TE buffer compared to 100% ethanol used in Example 1.

Example 3

In accordance with the procedures of Example 1 except that Daitomaceus Earth (Bio RAD Co & Ltd.), glass powder (Riken), porous-high surface glass (Bio101) or an anion ion-exchange resin (Qiagen) was used instead of the glass filters, 4–6 μg of the plasmid DNA was obtained for each carrier. Since 4–6 μg of the plasmid DNA is maximum yield from 0.6 ml of the culture medium, the above yield of the plasmid DNA was the same as that of Example 1. Yield of plasmid DNA per mg of carrier is proportional to the surface area of the carrier and yield efficiency per 10 mg of carrier is listed in the table below.

| | |
|---|---|
| Diatomaceus Earth (Bio RAD Co & Ltd.) | 15–20 μg |
| Glass powder (Riken) | 5 μg |
| Porous-high surface glass (Bio101) | 10–20 μg |
| Anion ion-exchange resin (Qiagen) | 5 μg |

What is claimed is:

1. A method for collecting plasmid DNA by lysing microbial cells, adsorbing released plasmid DNA on a carrier and collecting the DNA adsorbed on the carrier, which method comprises the following steps of:

lysing the microbial cells on a carrier in the form of mesh filter, wherein said carrier is selected from the group consisting of glasses, silica gels, celite and Diatomaceous Earth, by successively adding a solution for lysing cells and a solution for DNA adsorption to the microbial cells while keeping solutions on the carrier so that the plasmid DNAs obtained by lysing cells are adsorbed onto the carrier, separating solutions used for lysing cells and adsorbing DNAs from the carrier, eluting the plasmid DNAs adsorbed on the carrier with a solution for eluting plasmid DNAs and collected the eluted plasmid DNAs.

2. The method of claim 1 wherein the solution for DNA adsorption is a solution containing chaotropic ions (Solution IV).

3. The method of claim 1 wherein the carrier is washed and dried before the elution with the solution for eluting DNA.

4. The method according to claim 1, wherein the solution for eluting plasmid DNAs is a low salt buffer that contains no alkaline.

5. The method of claim 1 wherein the solution for lysing cells comprises a solution for degrading microbial cell walls (Solution I), a solution of alkaline-ionizable surfactant (Solution II) and a neutralization solution (Solution III).

6. The method of claim 5 wherein Solution I is an aqueous solution of Tris/EDTA/glucose/lysozyme, Solution II is an aqueous solution of NaOH/SDS and Solution III is an aqueous solution of potassium acetate.

7. The method of claim 5 wherein Solution I contains an RNase.

8. The method of claim 1 wherein a solution for lysing cells and a solution for neutralization and DNA adsorption are added successively to the microbial cells so that the DNA is adsorbed on the carrier.

9. The method of claim 8 wherein pH of the solution for neutralization and DNA adsorption is adjusted to a range of 6–12.

10. The method of claim 8 wherein the solution for lysing microbial cells comprises a solution for degrading microbial cell walls (solution I) and a solution of alkaline-ionizable surfactant (Solution II), the solution for neutralization and DNA adsorption is a single solution containing a neutralizer and chaotropic ions.

11. The method of claim 10 wherein Solution I is an aqueous solution of Tris/EDTA/glucose/lysozyme, Solution II is an aqueous solution of NaOH/SDS and the solution for neutralization and DNA adsorption is a solution containing potassium acetate and chaotropic ions.

12. The method of claim 10 wherein Solution I contains an RNase.

13. A method for collecting plasmid DNAs by lysing microbial cells, adsorbing released plasmid DNAs on a carrier selected from the group consisting of glasses, silica gels, celite and Diatomaceous Earth and collecting the DNAs adsorbed on the carrier, which method comprises the following steps of:

feeding microbial cells into a column comprising the carrier provided on a membrane filter capable of retaining a solution and permeating the solution when aspirated, lysing the microbial cells in the column by successively adding a solution for lysing cells and a solution for DNA adsorption to the microbial cells while keeping solutions in the column so that the DNA obtained by lysing cells is adsorbed onto the carrier, separating solutions used for lysing cells and adsorbing DNAs from the column by aspiration, and feeding a solution for eluting plasmid DNA into the column and aspirating to collect the plasmid DNA adsorbed on the carrier.

14. The method of claim 13 wherein the feeding of the microbial cells is performed by feeding a culture broth containing microbial cells and then aspirating so that the microbial cells are trapped by the membrane filter.

15. The method of claim 13 wherein the carrier is washed and dried before the elution with the solution for eluting DNA.

16. The method of claim 13 wherein the carrier is in the form of mesh filter, beads or powder.

17. The method according to claim 13, wherein the solution for eluting plasmid DNAs is a low salt buffer that contains no alkaline.

18. The method of claim 13 wherein the solution for lysing cells comprises a solution for degrading microbial cell walls (Solution I), a solution of alkaline-ionizable surfactant (Solution II) and a neutralization solution (Solution III), and the solution for DNA adsorption is a solution containing chaotropic ions (Solution IV).

19. The method of claim 18 wherein Solution I is an aqueous solution of Tris/EDTA/glucose/lysozyme, Solution II is an aqueous solution of NaOH/SDS and Solution III is an aqueous solution of potassium acetate.

20. The method of claim 18 wherein Solution I contains an RNase.

21. The method of claim 13 wherein a solution for lysing cells and a solution for neutralization and DNA adsorption are added successively to the microbial cells so that the DNA is adsorbed on the carrier.

22. The method of claim 21 wherein pH of the solution for neutralization and DNA adsorption is adjusted to a range of 6–12.

23. The method of claim 21 wherein the solution for lysing microbial cells comprises a solution for degrading microbial cell walls (Solution I) and a solution of alkaline-ionizable surfactant (Solution II), the solution for neutralization and DNA adsorption is a single solution containing a neutralizer and chaotropic ions.

24. The method of claim 23 is wherein Solution I is an aqueous solution of Tris/EDTA/glucose/lysozyme, Solution II is an aqueous solution of NaOH/SDS and the solution for neutralization and DNA adsorption is a solution containing potassium acetate and chaotropic ions.

25. The method of claim 23 wherein Solution I contains an RNase.

* * * * *